United States Patent [19]

Genova et al.

[11] Patent Number: 4,990,513

[45] Date of Patent: Feb. 5, 1991

[54] ANTIHYPOXIC DRUG AND METHOD OF ITS APPLICATION

[75] Inventors: Ani I. Genova; Milka P. Nikolova; Maria G. Todorova; Alexander P. Monov; Nikola G. Alexandrov; Rumen K. Nikolov; Violeta H. Andonova; Nadejda I. Zoneva; Yosif N. Nisimov; Snejana G. Vitkova; Nikola G. Boyadjiev; Anastasia M. Stoyanova; Keranka N. Savova; Nevena L. Firkova; Slava N. Spasova, all of Sofia, Bulgaria

[73] Assignee: S O "Pharmachim", Sofia, United Kingdom

[21] Appl. No.: 10,369

[22] Filed: Feb. 3, 1987

[51] Int. Cl.$^5$ .............................................. A61K 31/505
[52] U.S. Cl. .................................. 514/274; 514/256; 514/425
[58] Field of Search ........................ 514/274, 256, 425

[56] References Cited

FOREIGN PATENT DOCUMENTS 1039113 8/1966 United Kingdom .

OTHER PUBLICATIONS

Psychopharmacol., 1977, 53, pp. 72-78—Krug.

Primary Examiner—Frederick E. Waddell
Attorney, Agent, or Firm—Klein & Vibber

[57] ABSTRACT

The antihypoxic drug with verebroprotective and hepatoprotective action contains piracetam and orotic acid or their pharmaceutically tolerable salts in a weight ratio of from 500:1 to 1:2. This combined drug is administered for the treatment of acute and chronic diseases and exogenic intoxications in daily doses respectively from 0.150 to 50 g and from 0.030 to 0.30 g of both components. The synergistic effect of the combination is shown in the antihypoxic action as confirmed by clinical data. The drug can be administered orally or parenterally. The oral therapy comprises tablets, capsules, pills, solutions and emulsions and is applied in slight forms of exogenic intoxications, whereas the parenterally therapy is suitable in case of severe diseases and acute exogenic intoxications leading to complex injuries of the organism.

4 Claims, No Drawings

ANTIHYPOXIC DRUG AND METHOD OF ITS APPLICATION

FIELD OF THE INVENTION

The invention relates to a antihypoxic drug and in particular to a drug with cerebroprotective and hepatoprotective action as well as to its application in the treatment of acute and chronic diseases and intoxications leading to complex injuries of the entire organism.

DESCRIPTION OF THE PRIOR ART

It is known that orotic acid representing uracyl-4-carbonic acid or vitamin $B_{13}$ exhibits a protective action in cases of different liver intoxications and injuries in exerting a vitamin-like action and assisting the anabolic, detoxic and regenerative functions of the liver cell. The orotic acid exerts a weak antihypoxic action. See Krug, M. et al, Psychopharmacol., 1977, 53, p. 72–78.

It is also known that 2-oxo-pyrrolidine-1-acetamide is a no-otropic preparation with generic name piracetam that is exerting a beneficial effect on disease disturbances of memorizing processes and learning capacity in case of different injuries of the central nervous system as for example perturbation of memory, reduced retaining ability, metal fatigue, comatous state and acute psychic disturbances of intoxication nature, alcohol delirium etc. See G. B. Patent No.. 1,039,113.

In case of independent application orotic acid has a weak antihypoxic effect on liver parenhym and a still weaker effect on the central nervous system.

SUMMARY OF THE INVENTION

The object of the invention is to provide an antihypoxic drug and in particular a drug with cerebroprotective and hepatoprotective action as well as a method of its application in cases of combined acute and chronic diseases and intoxications in order to achieve an increased antihypoxic effect.

This object is attained by an antihypoxic drug and in particular a drug with cerebroprotective and hepatoprotective action that comprises piracetam and orotic acid or their pharmaceutically tolerated salts in weight ratio of 500:1 to 1:2.

It has been established that in simultaneous application of piracetam and orotic acid both components interact exclusively beneficially resulting in a higher antihypoxic effect compared to the single effect of these preparations. The synergistic effect of the combination according to the invention expressed in potentiation of the antihypoxic effect that was confirmed by the results of pharmacological investigations as shown in Table I and by respective clinical data.

TABLE I

Antihypoxic effect of piracetam and orotic acid in a model of hypobaric hypoxia in mice.

| Substance | Dose, mg/kg | Increase in resistance to hypoxia, /%/ |
|---|---|---|
| Piracetam | 500 | 29 |
| Orotic acid | 25 | 5 |
| Piracetam + orotic acid | 500 + 25 | 76.6 |
| Piracetam | 1000 | 37.9 |
| Orotic acid | 50 | 9.7 |
| Piracetam + orotic acid | 1000 + 50 | 91.5 |

It is preferable to administer the drug according to the invention in the organism as a ready made drug.

DETAILED SPECIFICATION

The combination of active substances according to the invention is suitable for preparation of pharmaceutical compositions and preparations. The ready made dosage forms can contain the active substances or their pharmaceutically tolerable salts mixed to the usual to the pharmaceutical technology accessory substances and carriers as shown in the adduced examples.

The compositions according to the invention can be administered orally or parenterally whereby the latter is preferable in treating severe diseases and acute exogenic intoxications. The oral therapy that can be applied in form of tablets, capsules, pills, solutions and emulsions is suitable in slight forms of exogenic intoxications, for prophylactic purposes or after applications of parenteral forms in the acute phase of the disease.

Single doses of piracetam amount from 0.05 to 5 g.; of orotic acid from 0.01 to 0.1 g while the daily doses are respectively from 0.150 to 50 g and from 0.30 to 0.30 g. distributed in three to six administrations.

The investigations carried out on acute toxicity of the combination according to the invention show that when it is administered in doses of 2500 mg/kg intramuscularly, 1000 mg/kg intravenously and 3000 mg/kg intraperitionially, no toxic effects are observed thus proving that this combination is practically non-toxic. Phatomorphologic studies on subchronic one-month toxicity on rats treated with 100 mg/kg and 500 mg/kg intramuscularly display no pathologic changes of inner organs and haematological parameters. The combination does not provoke a local irritating effect at the site of administering.

The composition according to the invention was applied as a method for treatment of 15 patients with acute intoxications with vegetable toxins from falloid mushrooms that lead clinically and laboratorally to toxic injuries of liver. The results are displayed in the examples illustrating the invention.

It has been established that the drug according to the invention could be used in the case of several modern diseases and intoxications as well as in case of some complex influences on human organism of ecologic nature accompanied by pathologic changes and deviations, expressed appearance of acute and chronic hypoxia that is affecting the central nervous system, the liver and other organs and systems where it is necessary to exert a simultaneous action on the liver and the brain.

The advantages of the antihypoxic drug according to the invention are the following: an increased antihypoxic effect is produced that is manifested simultaneously in case of cerebral and hepatic injuries being interrelated in case of diseases and acute or chronic intoxications. The administering of the combination as a ready made drug form permits a rapid and safe use of different doses of the components in the most beneficial synergistic ratio thus reducing the possibility for development of secondary effects of endogenous products forming in many cases of hepatic diseases and intoxications that cause injuries of secondary character in the cerebral structures. In administering the drug can be reduced by 30% the average daily dose of piracetam compared to its individual application. Further on is shortened the total period of treatment and is avoided the danger of complications.

DETAILED EXAMPLES THAT ILLUSTRATE THE INVENTION

The following examples better illustrate the invention:

EXAMPLE 1

Pharmacological Test

Antihypoxic effect after model of hypobaric hypoxia of mice (method of Nakanishi).

The experiments are carried out on 60 White mice, line H (distributed in groups of 10 animals each), in a glass hermetic vessel. The pressure of the air is reduced abruptly by means of a vacuum pump down to 210 mm Hg. corresponding to 10,000 m altitude above sea level. The drug combination is administered intraperitonially 30 min prior to the beginning of hypoxia. Life duration of the mice is recorded in seconds. The results from the experimental groups are recorded as percentage change with regard to the control group/table 1/. From the table it is seen that in combining 500 mg/kg piracetam with 25 mg/kg orotic acid, the superadditive effect of antihypoxic action is 42.6% while with the combination of 1000 mg/kg piracetam and 50 mg/kg orotic acid this superadditive antihypoxic effect amounts to 43.9%.

EXAMPLE 2

Clinical Data

Patient G.D.G., 19 years old file No.. 21648/1984, Hospital for first aid, Medical Institute "N.Pirogov", date of entrance—4.10.1984 and date of discharge—5.11.1984.

Diagnosis: Mycetismus Intox. phaloides, Gastroenterocolitis acuta, Hepatopatia toxica, Encephalopatia toxica.

Excerpt from anamnesis, status and investigations: Together with three friends he consumed wild-growing mushrooms, prepared on open fire. After a latent period of 6–7 hours appear the first symptoms of intoxication characteristic for toxic gastroenterocolitis: nausea, vomiting, diarrhea, general toxic manifestations—weakness, vertigo, feebleness and hepato-toxic manifestations—strain and pains in the right subcostal region, increase in liver size up to 3–4 cm below the costal arc. The pulse at the time of entering the hospital was 108/min and the arterial pressure re 120/80. Some of the analysis data are as follows:

|  | Date | | | | |
|---|---|---|---|---|---|
|  | 4.10.84 | 5.10.84 | 6.10.84 | 10.10.84 | 31.10.84 |
| SGOT,U/l | 80 | 86 | 22 | 11 | 6 |
| SGOT,U/l | 23 | over 86 | 77 | 58 | 2 |
| Ser.Bilirub. (umol/l) | 39.31 | 27.9 | 18.6 | 25.9 | 17 |

The treatment comprised stomach lavage, forced diuresis, hyperbaric oxygenation, general detoxicating means, and piracetam in dose up to 4 g daily and orotic acid—two times 1 ml of 1% solution, intramuscularly. The patient was discharged as clinically healthy.

EXAMPLE 3

Patient I.T.N., 19 years old, file No.. 21650/1984, Medical Institute "N. Pirogov", entered on 4.10.1984 and discharged on 19.10.1984.

Diagnosis: Mycetismus Intox.phaloides, Gastroenterocolitis acuta. Hepatopatia toxica, Encephalopatia toxica.

Excerpt from anamnesis, status and investigations: Together with three friends he has consumed wild-growing mushrooms, prepared on open fire. After a latent period of 7–8 hours appear the symptoms of toxic gastroenterocolitis: nausea, vomiting, diarrhea, general toxic symptoms as feebleness, vertigo and hepatotoxic symptoms as strain and pains in the right subcostal region, increase in liver size by 2–3 cm below the costal arc. The pulse at moment of entering was 96/min. and arterial blood pressure 100/60. Some of the data from analysis are as follows:

|  | Date | | | | |
|---|---|---|---|---|---|
|  | 4.10.84 | 5.10.84 | 6.10.84 | 7.10.84 | 18.10.84 |
| SGOT,U/l | 36 | 47 | 47 | 17 | 4 |
| Ser.Bilir. (umol/l) | 32.07 | 10.4 | 7.2 | 11.4 | 13.4 |
| urea,(umol/l) | 8.09 | — | — | — | 4.3 |
| SGPT,U/l | 33 | 37 | 40 | 7 | 2 |

The treatment comprises stomach lavage, forced diuresis, hyperbaric oxygenation, general detoxicating means, piracetam in dose of 4g daily and orotic acid two time 1 ml of 1% solution, administered intramuscularly during 10 days. The patient was discharged as clinically healthy.

EXAMPLE 4

Patient S.S.T., 19 years old, file No.. 21651/1984, Medical Institute "N. Pirogov"-Sofia, entered on 4.10.1984 and discharged on 24.10.1984.

Diagnosis: Mycetismus Intox.phaloides, Gastroenterocolitis acuta, Hepatopatia toxica, Encephalopatia toxica.

Due to similarity of data from anamnesis and status with the above mentioned examples are presented data only from more characteristic analysis:

|  | Date | | | | |
|---|---|---|---|---|---|
|  | 4.10.84 | 6.10.84 | 7.10.84 | 11.10.84 | 22.10.84 |
| SGOT,U/l | 24 | 43 | 36 | 13 | 10 |
| SGPT,U/l | 33 | 86 | 72 | 79 | 4 |
| Serum bilir. (umol/l) | 18.1 | 30.19 | 10.3 | 14.3 | 6.2 |

The treatment of the patient comprises stomach lavage, forced diuresis, hyperbaric oxygenation, general detoxicating means and piracetam 4g daily and orotic acid two times 1 ml of 1% solution, administered intramuscularly during 10 days. The patient was discharged as clinically healthy.

EXAMPLE 5

Patient I.E.I., file No.. 21647/1984, Medical Institute "N.Pirogov"-Sofia, entered on 4.10.1984 and discharged on 19.10.84.

Diagnosis: Mycetismus Intox.phaloides, Gastroenterocolitis acuta, Hepatopatia toxica.

Due to similarity in data from anamnesis and status with the aforementioned examples are given only characteristic data from analysis:

|  | Date | | | | | |
|---|---|---|---|---|---|---|
|  | 4.10.84 | 5.10.84 | 6.10.84 | 7.10.84 | 11.10.84 | 18.10.84 |
| SGOT, U/l | 80 | over 80 | 16 | 24 | 10 | 4 |
| SGPT, U/l | 46 | over 86 | 36 | 23 | 33 | 5 |
| Ser.bil-irub., (umol/l) | 28.08 | 16.55 | 32.1 | 25.9 | 14.5 | 15.5 |

The treatment comprises stomach lavage, forced diuresis, hyperbaric oxygenation, general detoxicating means, piracetam 4g daily and orotic acid 2 times 1 ml of 1% solution intramuscularly. The patient was discharged as clinically healthy.

EXAMPLE 6

The results from clinical testing of combined piracetam and orotic acid drug were carried out during the period from 5.08.85 to 04.12.85 in II neurological Clinic of Medical Academy in Sofia. 32 patients were treated, 21 of which in conditions of acute and chronic experiment and the other 11 in chronic experiment. The distribution of tested patients after sex and age is presented in Table 2 below.

TABLE II

| SEX | AGE | | | |
|---|---|---|---|---|
|  | below 40 | 41-50 | 51-60 | over 60 |
| Men | 2 | 5 | 5 | 2 |
| Women | 4 | 9 | 4 | 1 |
| Total | 6 | 14 | 9 | 3 |

The distribution after nosological units is presented on table 3.

TABLE III

| State after passed cerebral insult | 5 |
|---|---|
| Chronic and transient cerebro-vasicular insufficiency | 14 |
| Vasomotoric cephalgia | 10 |
| State after cerebral trauma | 2 |
| State after viral meningitis | 1 |
| Total | 32 |

DETAILED DESCRIPTION OF METHODS USED (a) Acute experiment, carried out with 21 patients: After recording back-ground rheograms (volume and differential/speed/right-side fronto-mostoidal and volume and speed longitudinal of left calf) was injected one ampule of 5 ml piracetam-orotic acid intramuscularly. The rheographic changes were observed at the same leads at 5,15,30,60 and 120 minutes after administering of the preparation.

In the quantitative analysis were taken as parameters: amplitude of rheographic wave/$h_1$/, dicrotic and diastolic indices, relative part of anacrote, rate of spreading of REG wave. After complete termination of these investigations all data obtained with be submitted to statistical processing. All patients after terminating the acute experiment were included in the chronical experiment.

(b) Chronic experiment: All patients were treated by administration of piracetam-orotic acid intramuscularly, one ampule two times daily at 8 and 16.30 o'clock. In the case of 9 patients the second administration of the drug (at 16.30) was perorally. The duration of treatment was from 10 to 29 days. In the chronic experiment were made rheographic studies prior to and after termination of the treatment period. The main results obtained can be presented as follows:

1. In case of 22 patients from 24 patients in all, having headache was observed complete disappearance or diminishing of cephalgic symptoms. The patients with vasomotoric cephalgia showed a diminishing or disappearance of the headache during the period of treatment or after its termination in 100% of all patients studied and investigated.

2. In 14 out of 19 patients was established diminishing in different degrees or disappearance of vertigo, figurating as on of the basic complaints.

3. 12 patients announced an increase in mental working ability, improved memorizing capacities and better fixing of attention capacity.

4. It is important to note that 6 patients with complaints of superficial, short sleep, insomnia informed the doctors that after administration of the second daily dose of the drug at 16.30 o'clock, they got an improved night sleep without taking any additional hypnotics or other medicines.

5. Two patients (men aged 46 and 52) informed the doctors of an improvement of their sexual potency.

6. There was no case of patients showing allergic, gastrointestinal or other side effects.

7. The beneficial effect of piracetam-orotic acid was confirmed with patients younger than 60 years and without strong rheographic modifications.

EXAMPLE 7

Drug composition

| A. Ampules | |
|---|---|
| Piracetam | 20 kg |
| Orotic acid | 1 kg |
| Ethanolamine | 0.80 kg |
| Citric acid | up to pH 5.5 to 6.5 |
| Water for injection | up to 100 l |
| B. Tablet dosage form | |
| Piracetam | 0.05 to 1.0 g |
| Orotic acid | 0.01 to 0.10 g |
| Micricrystallic cellulose | 0.05 to 0.10 g |
| Lactose | 0.05 to 0.10 g |
| Aerosil | 0.001 to 0.008 g |
| Talc | 0.003 to 0.006 g |
| Magnesium stearate | 0.002 to 0.004 g |
| C. Solid gelatine capsule | |
| Piracetam | 0.005 to 0.600 g |
| Orotic acid | 0.01 to 0.100 g |
| Microcrystallic cellulose | 0.05 to 0.100 g |
| Lactose | 0.05 to 0.100 g |
| High-molecular polymer | 0.001 to 0.05 g |
| Talc | 0.004 to 0.05 g |
| Magnesium stearate | 0.002 to 0.025 |

Although the invention has been described and illustrated with reference to a plurality of preferred embodiments thereof, it is to be expressly understood that it is in no way limited to the disclosure of such preferred embodiments but is capable of numerous modifications within the scope of the appended claims.

We claim:

1. An anti-hypoxic therapeutic composition in unit dosage form consisting essentially of an effective amount of 2-oxo-pyrrolidine-1-acetamide and orotic acid, or the pharmaceutically acceptable salts thereof, in a weight ratio of about 20:1.

2. A composition according to claim 1 in tablet form.

3. A method of treating headache, vertigo or insomnia, in a patient consisting essentially of the steps of:
orally or parenterally administering to a host afflicted by said disease an anti-hypoxic effective amount of a 2-oxo-pyrrolidine-1-acetamide and orotic acid, or the pharmaceutically acceptable salts thereof, in a weight ratio of about 20:1.

4. The treatment according to claim 3 consisting of administering in unit dosage form 2-oxo-pyrrolidine-1-acetamide in a dosage of up to 4 grams daily, in combination with orotic acid twice daily, in the form of one ml of 1% solution.

* * * * *